United States Patent [19]
Haber et al.

[11] Patent Number: 5,220,948
[45] Date of Patent: Jun. 22, 1993

[54] PRECISION SYRINGE-FILLING MECHANISM

[75] Inventors: Terry M. Haber, Lake Forest; William H. Smedley, Lake Elsinore; Clark B. Foster, Laguna Niguel, all of Calif.

[73] Assignee: Habley Medical Technology Corp., Laguna Hills, Calif.

[21] Appl. No.: 741,776

[22] Filed: Aug. 7, 1991

[51] Int. Cl.$^5$ .......................... B65B 1/04; A61M 5/00
[52] U.S. Cl. ...................................... 141/27; 141/384; 604/90; 604/210; 604/211; 604/416; 128/919
[58] Field of Search .................................. 604/82-92, 604/207-211, 416, 905; 128/919; 141/27, 18, 21, 346, 383, 384

[56] References Cited

U.S. PATENT DOCUMENTS

| | | | |
|---|---|---|---|
| 3,833,030 | 9/1974 | Waldbauer, Jr. et al. | 141/26 |
| 3,844,318 | 10/1974 | Raia et al. | 141/27 |
| 3,875,979 | 4/1975 | Hults | 604/208 |
| 3,907,009 | 9/1975 | Dobbins | 604/207 |
| 4,219,055 | 8/1980 | Wright | 604/208 |
| 4,252,159 | 2/1981 | Maki | 141/27 |
| 4,357,971 | 11/1982 | Friedman | 141/27 |
| 4,668,220 | 5/1967 | Hawrylenko | 604/209 |
| 4,778,454 | 10/1988 | La Dow | 141/27 |

FOREIGN PATENT DOCUMENTS 0458275  3/1951  Italy ..................... 604/209

Primary Examiner—C. Fred Rosenbaum
Assistant Examiner—Mark Bockelman
Attorney, Agent, or Firm—Townsend and Townsend

[57] ABSTRACT

A dosing assembly (80) is used to controllably fill a syringe (4), held within a syringe holder (50), from a vial (2) of the type including a piston (18) mounted within a container (14). The syringe holder (50) is threadably mounted (52, 36) to the vial with the needle cannula (72) piercing the piston to permit the syringe holder to be driven against the piston in a controlled manner to accurately meter the pharmaceutical introduced into the syringe. The dosing assembly includes a rotary drive (82, 88, 110, 118, 126) which rotates the syringe holder about the syringe holder axis, thus driving the syringe against the piston, as the syringe holder and syringe therewith are rotated about an axis situated 90° from the syringe axis. This causes the pharmaceutical within the vial to be forced through the needle cannula and into the syringe; the amount of the dose in the syringe depends upon how far the user rotates the syringe holder using the rotary drive.

10 Claims, 9 Drawing Sheets

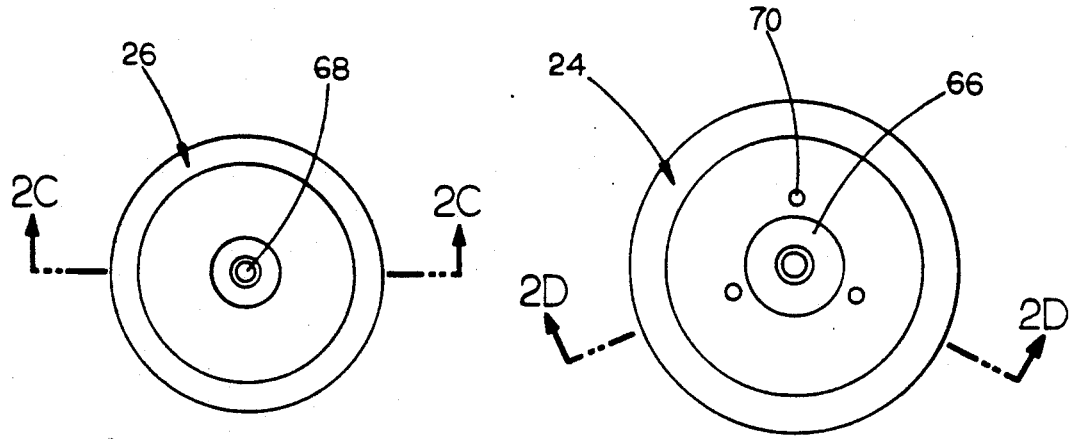
FIG. 2A
FIG. 2B
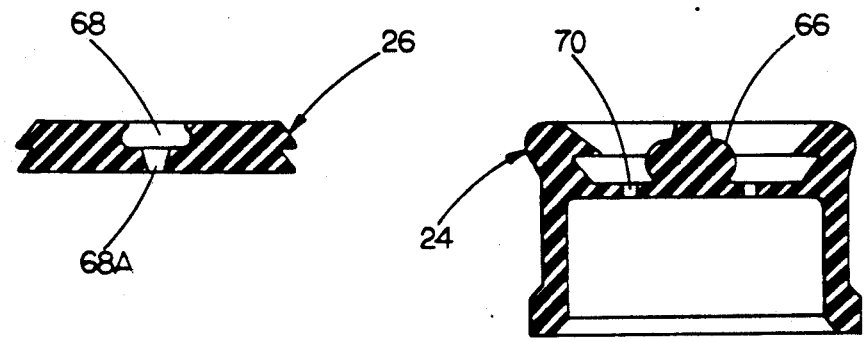
FIG. 2C
FIG. 2D
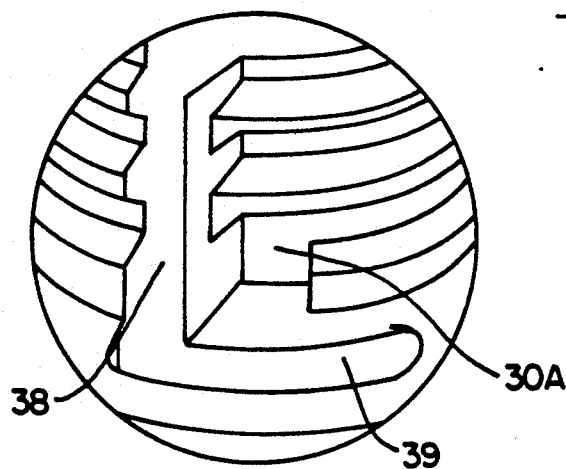
FIG. 2E

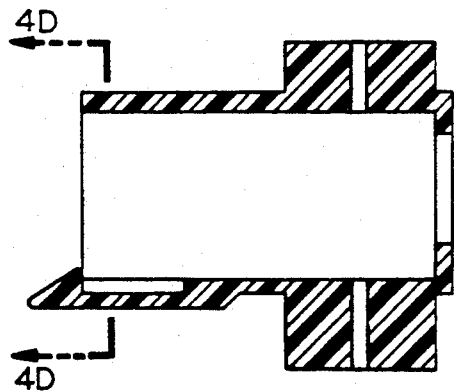
FIG 4C
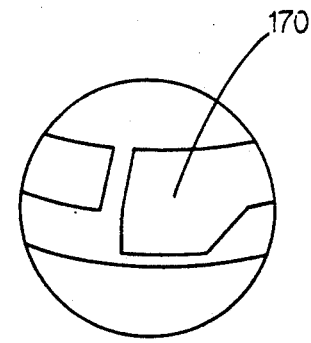
FIG 4F
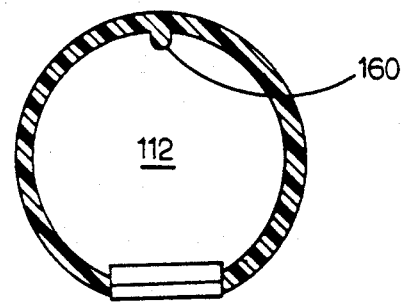
FIG 4D
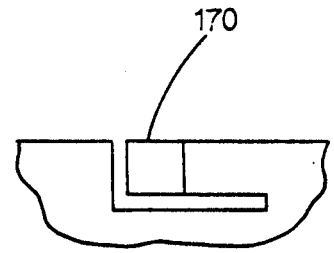
FIG 4G
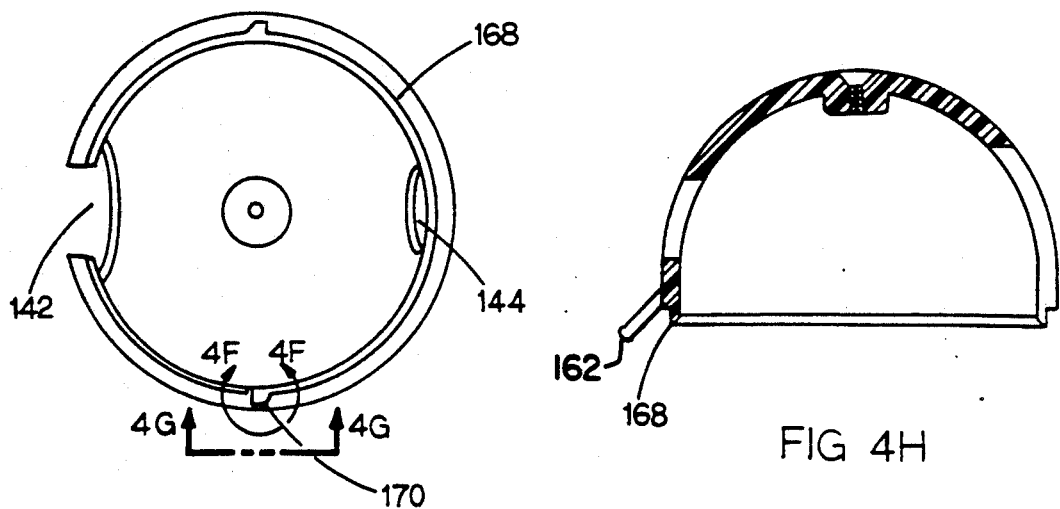
FIG 4E
FIG 4H

PRECISION SYRINGE-FILLING MECHANISM

CROSS-REFERENCE TO RELATED APPLICATIONS

This application is related to the following U.S. Patent Applications: U.S. patent application Ser. No. 07/741,777 for Syringe Filling and Metering Device for Pharmaceutical Containers still pending, U.S. patent application Ser. No. 07/741,779 for Controlled Action Self-Mixing Vial now U.S. Pat. No. 5,158,546 both being filed on the same day as this application, and U.S. patent application Ser. No. 07/615,610 filed Nov. 19, 1990 for Multi-Chamber Vial, now U.S. Pat. No. 5,114,411 the disclosures of which are incorporated by reference.

BACKGROUND OF THE INVENTION

Some patients, or their parents or guardians, must administer pharmaceuticals on a regular basis. For example, children being administered a human growth hormone must generally receive the medication daily. Medications such as human growth hormone are very expensive and are also very critical as to dose. Therefore, it is important that the amount of the medication aspirated into the syringe for each dose be precise. Since the person administering the pharmaceutical may not be medically trained, obtaining accurate, consistent injections is often difficult.

One problem associated with administering human growth hormone using conventional devices and procedures is the complexity involved. For example, one conventional technique requires 15 steps to reconstitute the growth hormone, 16 steps to fill a specially designed glass cartridge, 13 steps to insert the glass cartridge into a specially designed syringe, and 17 steps to inject the dose.

Another problem arises when administering a pharmaceutical to a child on a regular basis. Children do not want to feel that they are different; they do not want others to think they are different. The conventional devices used to prepare some pharmaceuticals, such as human growth hormone, tend to create a stigma of abnormality in the child who undergoes such medical treatment.

SUMMARY OF THE INVENTION

The present invention is directed to a precision syringe-filling mechanism, generally referred to as a dosing assembly, which houses a pharmaceutical-containing vial and a syringe. The dosing assembly includes a rotary drive which rotates a syringe holder, which holds the syringe to be filled, about the axis of the syringe holder, thus driving the syringe holder against the vial, as the vial and syringe therewith are rotated about a second axis, preferably situated 90° from the syringe axis.

The dosing assembly can be used with vials of different types. One type includes a pharmaceutical housed within a piston and cylinder arrangement, the piston being pierceable by a needle cannula of other conventional syringe. In this embodiment the axial movement of the syringe holder will tend to drive the piston down the cylinder or barrel of the vial, thus forcing the pharmaceutical through the needle cannula and into the syringe. Another type of vial could be in the form of a conventional cartridge used with conventional syringes. These cartridges include a cylindrical barrel having a septum at one end, a piston at the other end and the pharmaceutical between the two. Using this type of vial, the dosing assembly would include an elongate piston stop with an outer end positioned against the piston; the needle cannula would pass through the septum; the axial movement of the syringe holder would drive the barrel over the piston, the piston being held in place by the piston stop. The vial could also be in the form of a collapsing bellows type of container with a septum at one end; as the syringe holder moves axially against the bellows-type vial, the end of the vial opposite the septum is held in place so that the vial collapses to drive the pharmaceutical through the needle cannula and into the syringe.

One of the primary advantages of the invention is that filling the syringe is easily and accurately controlled, using the dosing assembly by which the syringe is driven towards the piston by rotating the syringe holder relative to the mixing vial within the dosing assembly. The present invention, especially when used with a controlled action mixing vial, greatly reduces the number of steps required to prepare for an injection of a pharmaceutical such as human growth hormone. This not only simplifies the procedure and makes it less imposing, it also can substantially reduce the possibility of error.

The manipulation of the dosing assembly provides both audible and tactile feedback to the user as to the amount of the pharmaceutical being delivered because of the use of detents. The invention is thus specially suited for visually impaired persons and persons who may have lost a degree of manual dexterity. There are no small knobs to rotate to try to determine the metered dose. Rather, the manipulation is of a relatively large control dome which can be easily grasped by user with even limited manual dexterity. The audible feedback permits even persons who have lost all or part of their sight to accurately fill the syringe for a proper dose.

Other features and advantages of the invention will appear from the following description in which the preferred embodiment has been set forth in detail in conjunction with the accompanying drawings.

BRIEF DESCRIPTION OF THE DRAWINGS

FIG. 2A is a view of the plastic insert of FIG. 2 taken along line 2A—2A;

FIG. 2B is a view of the elastomeric seal of FIG. 2 taken along line 2B—2B;

FIGS. 2C and 2D are cross-sectional views taken along lines 2C—2C and 2D—2D in FIGS. 2A and 2B, respectively;

FIG. 2E is an enlarged view of the spring element formed in the threaded driver showing the region between the two outermost threads being filled in to act as a detent;

FIG. 4C is an enlarged cross-sectional view of the carriage of FIG. 4;

FIG. 4D is a cross-sectional view taken along line 4D—4D of FIG. 4C;

FIG. 4E is an enlarged bottom view of the control dome of FIG. 4;

FIG. 4F is an enlarged view taken along line 4F—4F of FIG. 4E;

FIG. 4G is an enlarged view taken along line 4G—4G of FIG. 4F;

FIG. 4H is a cross-sectional view of the control dome of FIG. 4;

DESCRIPTION OF THE PREFERRED EMBODIMENT

The present invention can be used with a variety of pharmaceutical-containing containers which permit their contents to be accessed by a needle cannula and to be drawn out of the container, preferably without the introduction of any air into the pharmaceutical container. Since the present invention finds particular utility when used for administering human growth hormone, a controlled action mixing vial 2 will be first described because of its particular suitability for reconstituting two components which make up the human growth hormone.

Figure 1:
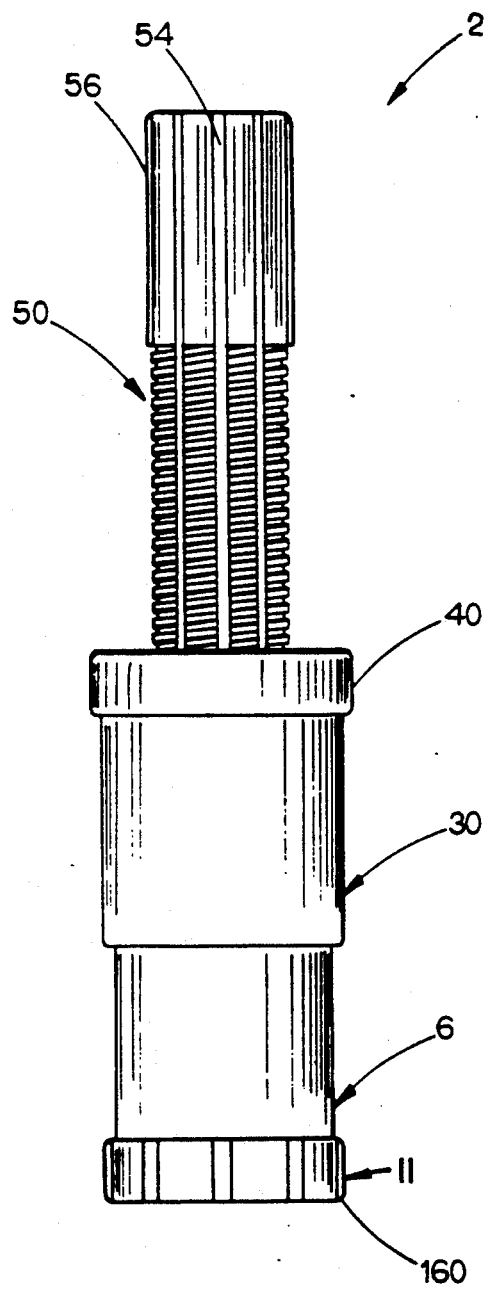
FIG. 1 is a side view of a controlled action mixing vial which is especially suited for us with the invention.
Figure 2:
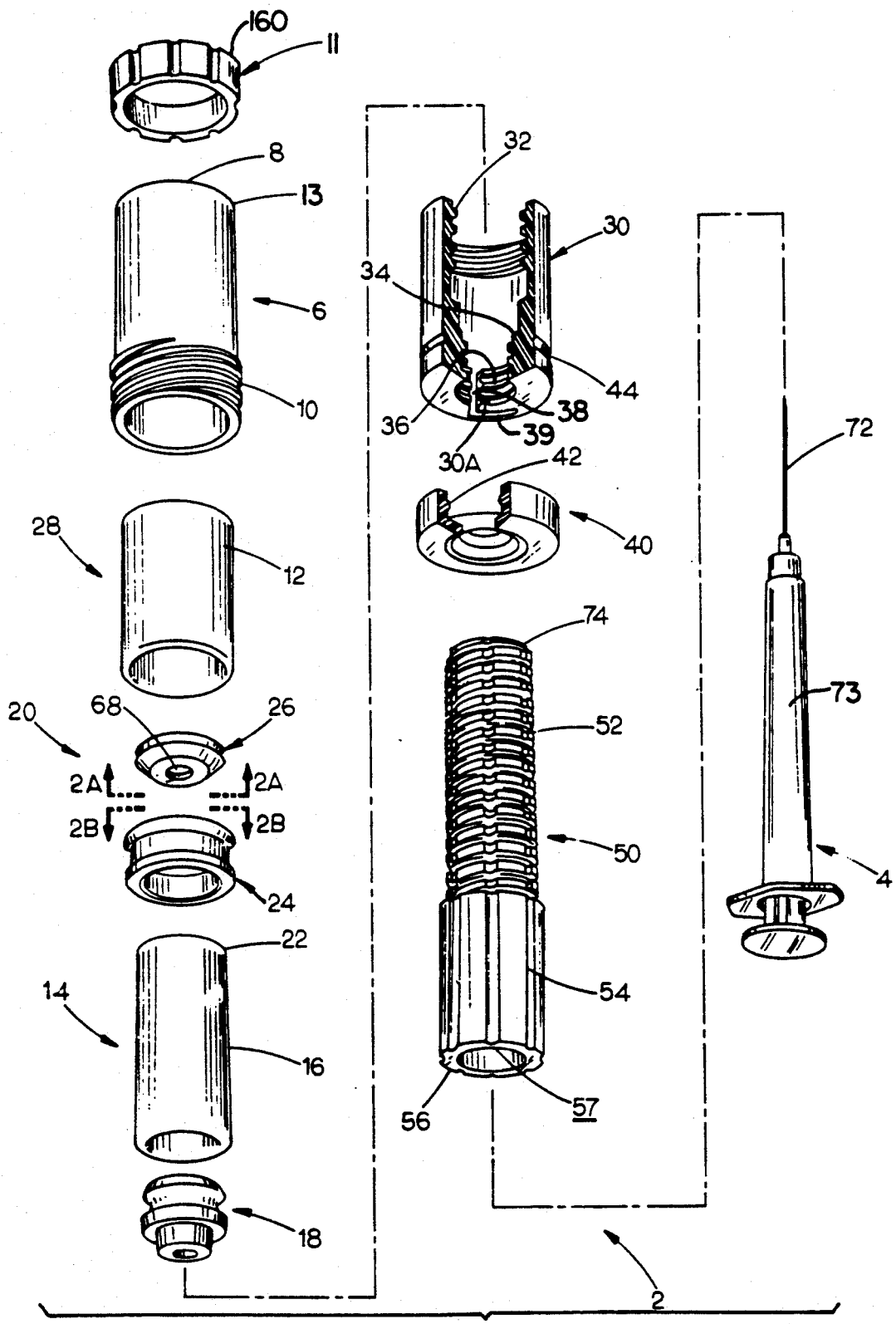
FIG. 2 is an exploded cross-sectional view of the mixing vial of FIG. 1, shown together with a conventional syringe.
Figures 3A, 3B, 3C:
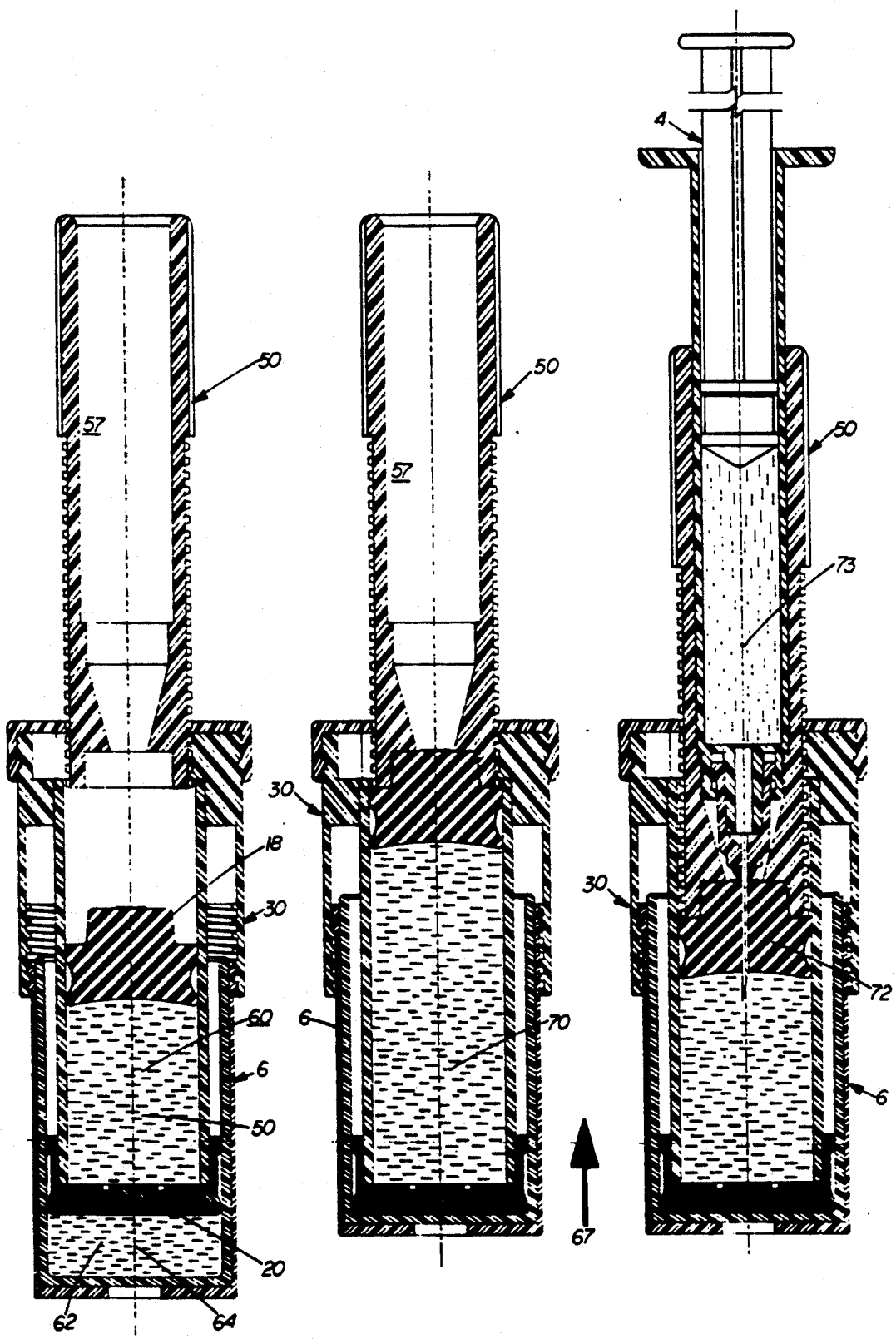
FIG. 3A is a cross-sectional view of the mixing vial of FIG. 1 in a pre-mixed condition.
FIG. 3B illustrates the mixing Vial of FIG. 3A after the supplemental container has been collapsed, placing the mixing vial in a post-mixed condition by screwing the two containers together, thereby mixing the pharmaceuticals in a relatively slow, controlled manner.
FIG. 3C shows the mixing vial of FIG. 3B in a post-aspiration condition with a syringe mounted within the syringe holder, the needle cannula of the syringe passing through the piston and the syringe holder with the syringe having been threaded into the mixing container driving the piston down the mixing container, thus causing a measured quantity of the mixed pharmaceutical within the mixing container to be forced into the syringe.

FIGS. 1, 2 and 3A illustrate a controlled action mixing vial 2 used with a generally conventional syringe 4. Mixing vial 2 includes a cylindrical cup housing 6, having a hole 8 at one end and external threads 10 at the other end. Cup housing 6 is made of a clear, shatter resistant plastic, such as radiation sterilizable acrylic or polycarbonate, and is sized to house a glass cup 12. The fit of glass cup 12 within cup housing 6 is quite snug so that hole 8 permits any air trapped within cup housing 6 to escape during assembly with glass cup 12. A cap 11 is secured to end 13 of cup housing 6 to provide a good gripping surface for the purposes discussed below.

Mixing vial 2 also includes a mixing container 14 made of a glass cylinder 16 housing pharmaceutically compatible elastomeric piston 18 and barrier seal 20 at inner end of 22 of cylinder 16. Barrier seal 20 includes an elastomeric seal 24 and a plastic insert 26. See FIGS. 2A–2D. Barrier seal 20 and glass cup 12 combine to create a supplemental container 28.

Mixing container 14 is threadably coupled to supplemental container 28 using a threaded driver 30. Threaded driver 30 includes internal threads 32, which engage external threads 10 of cup housing 6, and an annular shoulder 34 adjacent a second set of internal threads 36. Thus, rotating threaded driver 30 with respect to cup housing 6 in a clockwise direction will cause threaded driver 30 to be driven over cup housing 6, thus forcing mixing container 14 into supplemental container 28, as will be discussed below with reference to FIGS. 3A and 3B.

Mixing vial 2 also includes a ring 40 having an internal circular rib 42 which engages an external circular groove 44 formed on the outside of threaded driver 30 in the region surrounding internal threads 36. Ring 40 has calibration markings on its outside surfaces to allow a user to zero vial 2 between uses by rotating the ring.

Mixing vial 2 also includes a syringe holder 50 having external threads 52 along about half of its length sized to mate with internal threads 36 of threaded driver 30. Syringe holder 50 also includes a number of axially extending grooves 54 formed along its entire length. Grooves 54 are used to rotate syringe holder 50, either manually or through the use of additional structure described below. Threaded driver 20 includes an integrally formed spring 30A created by an axially extending groove 38 cut into threads 36 and a slot 39 extending circumferentially from groove 38. The region between the two outermost threads 36 adjacent groove 38 is filled in, see FIG. 2E, so to create a detenting action as spring 30A passes each groove 54 formed in threads 52. The interior 57 of syringe holder 50 is sized to accommodate syringe 4.

FIG. 3A illustrates mixing vial 2 in its pre-mixed condition with a first pharmaceutical 58 housed within a first variable volume region 60 defined within glass cylinder 16 between barrier seal 20 and elastomeric piston 18. A second pharmaceutical 62 is housed within a second variable volume region 64 defined within glass cup 12 and bounded by barrier seal 20.

In FIG. 3A first and second pharmaceuticals 58, 62 are shown as liquid pharmaceuticals. However, first variable volume region 60 could contain a dry pharmaceutical in, for example, a powdered or crystalline form.

FIG. 3B illustrates mixing vial 2 in its post-mixed condition after threaded driver 30 has been threaded onto cup housing 6 forcing barrier seal 20 farther into glass cup 12. Doing so causes the center portion 66 of elastomeric seal 24 to move in the direction of arrow 67 to a dashed-line position in FIG. 3B and become disengaged from within a hollow portion 68 of plastic insert 26. This permits fluid flow from second variable volume region 64, through hole 68A, through hollow portion 68 and through openings 76 formed in elastomeric seal 24 surrounding center portion 66. Other types of rupturable barriers could be used as well.

To access the mixed pharmaceutical 70, syringe 4 is inserted into interior 57 of syringe holder 50 until the syringe is fully within syringe holder 50 and the needle cannula 72 of the syringe has fully pierced elastomeric piston 18 as shown in FIG. 3C. Mixed pharmaceutical 70 is forced from first variable volume region 60 into the interior 73 of syringe 4 by rotating syringe holder 50 clockwise. This causes the inner end 74 of syringe holder 50 to drive elastomeric piston 18 from the post-mixed position of FIG. 3B, that is downwardly in FIG. 3C. This permits a very accurately controlled amount of mixed pharmaceutical 70 to be forced into syringe 4 according to the number of complete and partial rotations of syringe holder 50.

Figure 4:
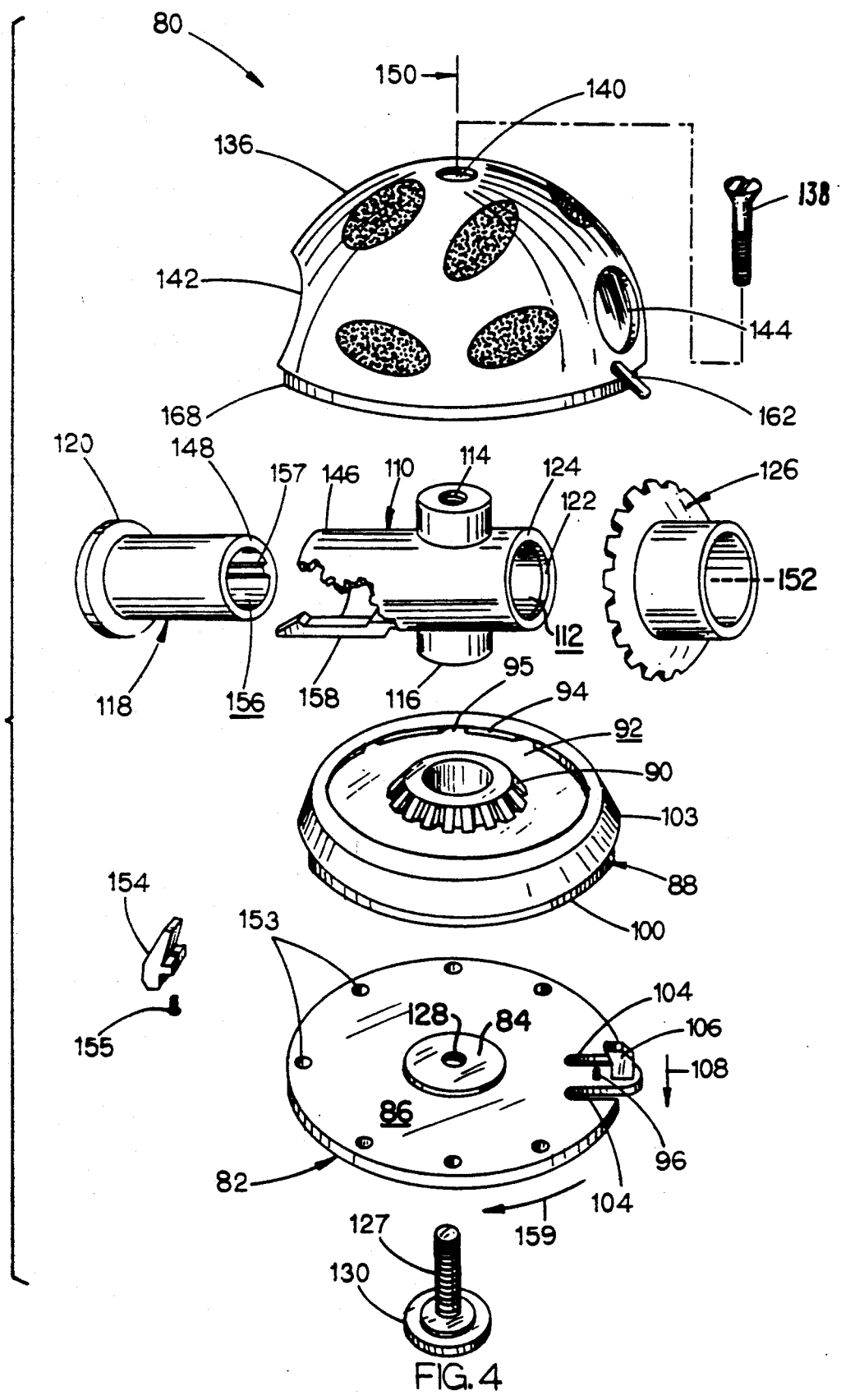
FIG. 4 is an exploded isometric view of a dosing assembly used with the mixing vial and syringe of FIGS. 2 and 3C.
Figure 4A:
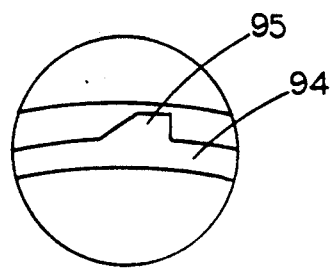
FIG. 4A is an enlarged top view of a portion of the base of FIG. 4 showing the detent in the annular groove.
Figure 5:
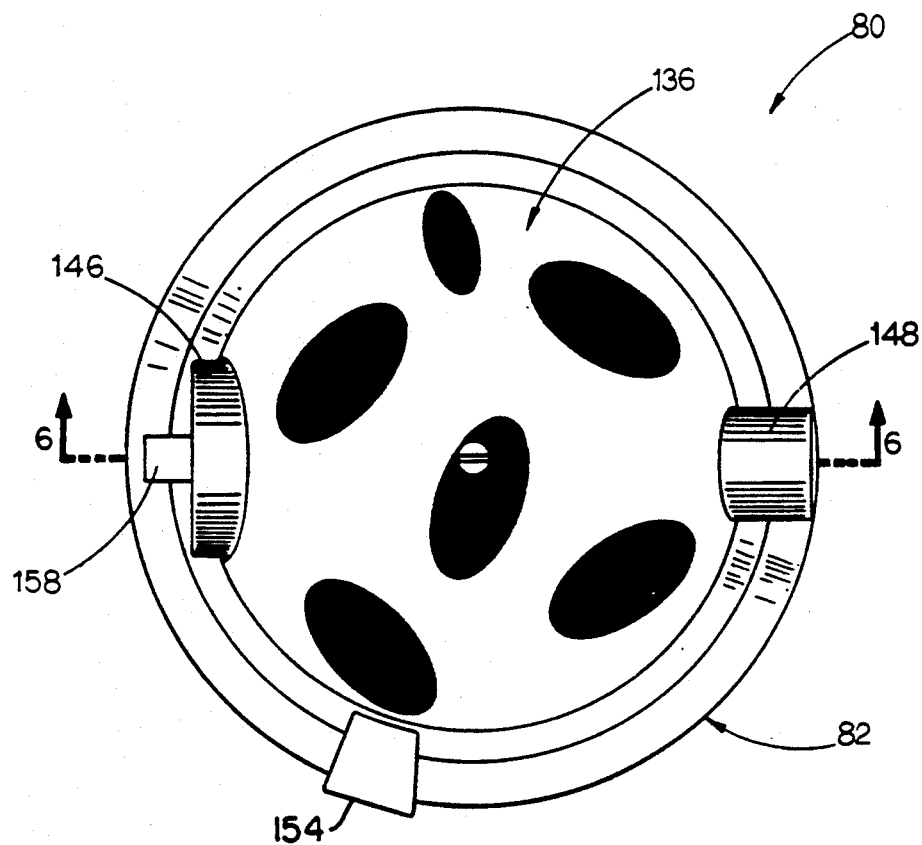
FIG. 5 is a top view of the assembled dosing assembly of FIG. 4.
Figure 6:
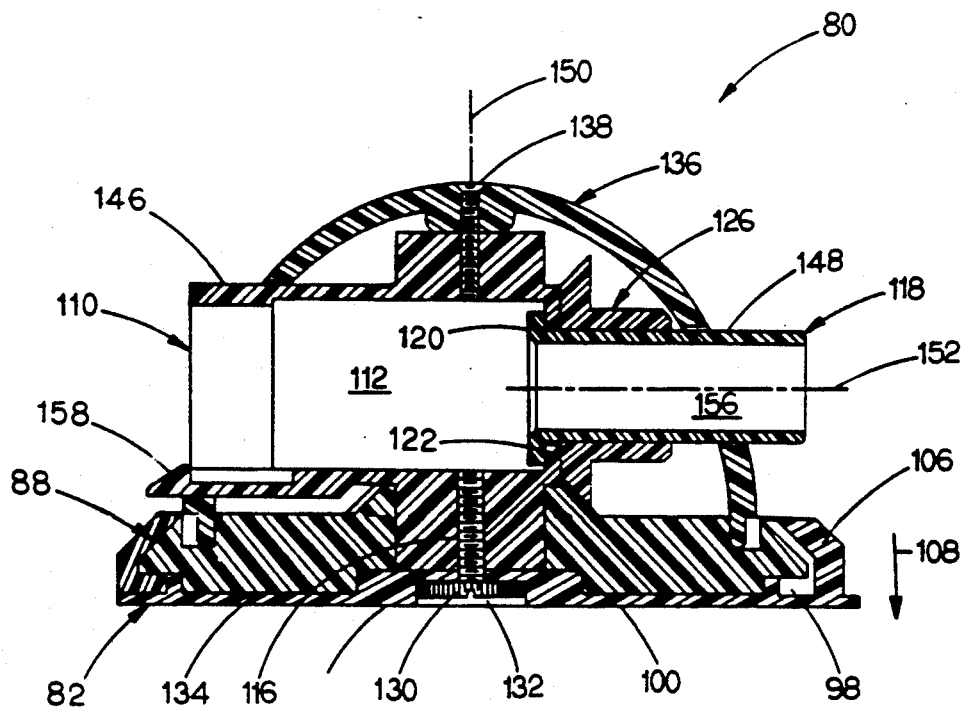
FIG. 6 is a cross-sectional view taken along line 6—6 of FIG. 5.

Controlled action mixing vial 2 is advantageously used in combination with a dosing assembly 80 illustrated in FIGS. 4–6. Assembly 80 includes a circular dosing plate 82, having a center circular pad 84 extending upwardly from a support surface 86. A circular base 88 is mounted to and is supported by dosing plate 82. Base 88 has an integral 45° bevel gear 90 extending from its upper surface 92 and an annular groove 94 formed in upper surface 92. Annular groove 94 has eight equally spaced, radially extending tapered receptacles 95 used as detents as discussed below. Base 88 is generally freely rotatable when mounted to dosing plate 82. However, dosing plate 82 includes an upwardly extending limit pin 96, which passes within an annular groove 98 formed in the underside 100 of base 88 about the periphery. Eight evenly spaced, radially extending slots 102 are formed in bottom 100 extending inwardly from groove 98. Slots 102 are positioned beneath receptacles 95 and are provided to engage pin 96. Groove 98 is sized to permit limit pin 96 to pass freely within groove 98 as base 88 rotates. Dosing plate 82 is made of a resilient plastic material, such as styrene or polycarbonate or ABS, and has a pair of relief slots 104 formed on either side of limiting pin 96. This permits the user to press down on an extension 106 in the direction of arrow 108 of FIG. 6 for reasons discussed below.

Dosing assembly 80 also includes a generally T-shaped carriage 110, having a horizontal bore 112 and upper and lower threaded bores 114, 116. Horizontal bore 112 is sized to accept a generally cylindrical guide drive 118, drive 118 having an outwardly extending flange 120 at one end. Flange 120 is sized to engage an inwardly extending flange 122 at one end 124 of bore 112 as shown in FIG. 6. A 45° bevel gear 126 is secured to guide drive 118, such as with an adhesive, to capture flange 122 between flange 120 and bevel gear 126. The combination of carriage 110, guide drive 118 and bevel gear 126 are rotatably mounted to circular pad 84 using a screw 127, which passes through a hole 128 in circular pad 84 and engages threaded bore 116 of carriage 110. Screw 126 has an enlarged head 130, which is housed within a countersunk hole 132 formed in the bottom 134 of dosing plate 82. Base 88 is securely but freely rotatably mounted to dosing plate 82.

A hemispherical control dome 136 is secured to carriage 110 by a screw 138 which passes through a center hole 140 formed in control dome 136 to engage threaded bore 114. Control dome 136 includes cut outs 142, 144, see FIGS. 4E, 4H, through which an end 146 of carriage 110 and end at 148 of guide drive 118 to pass respectively. Thus, rotating control dome 136 about axis 150 of dosing assembly 80 causes carriage 110 to rotate about axis 150 as well. Since bevel gears 126, 90 are engaged in this assembled condition, such rotation about axis 150 causes bevel gear 126 to rotate about its axis 152, which corresponds to the axis of guide drive 118. Gears 90, 126 are designed so that one full rotation of control dome 136 causes gear 126 to rotate one time.

To provide an aid for regulating the dose by limiting the rotary movement of control dome 136 about axis 150, a dose limiter 154 is secured to a desired position along the periphery of dosing plate 82 using a screw 155 which engages one of seven threaded holes 153 spaced apart along the periphery of plate 82.

Figure 4B:
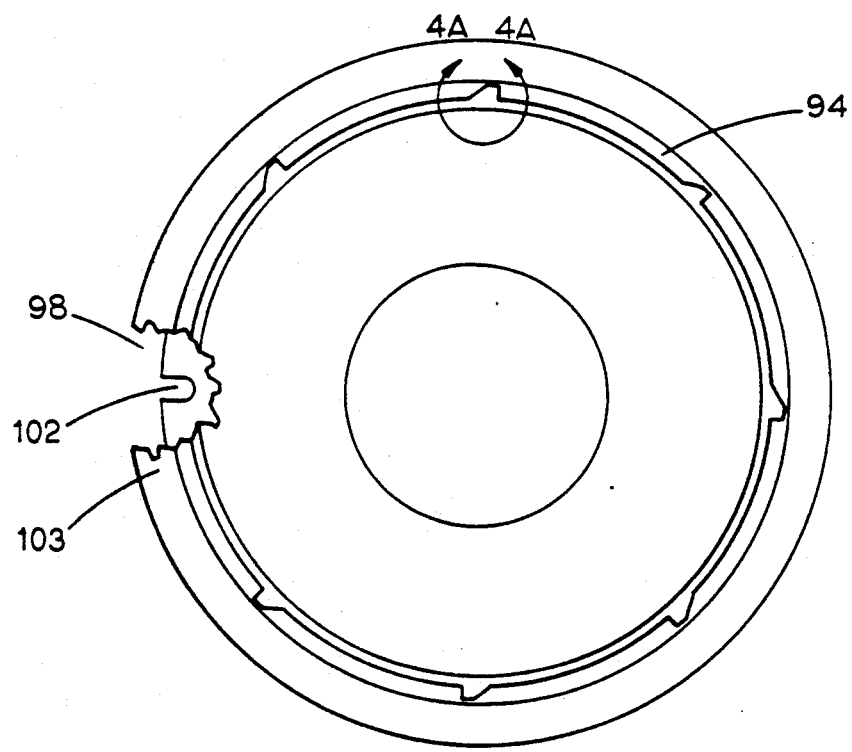
FIG. 4B is an enlarged top view of a portion of the base of FIG. 4 with a portion broken away to show the peripheral groove and radial slot formed in the bottom of the base.

Dosing plate 82 is rotated in the direction of arrow 159 (see FIG. 4) by first deflecting extension 106 in the direction of arrow 108 until pin 96 clears slots 102 (see FIG. 4B). Dosing plate 82 rotation is limited by the engagement of dose limiter 154 with a dome pin 162; see FIGS. 4 and 4H.

Figure 7:
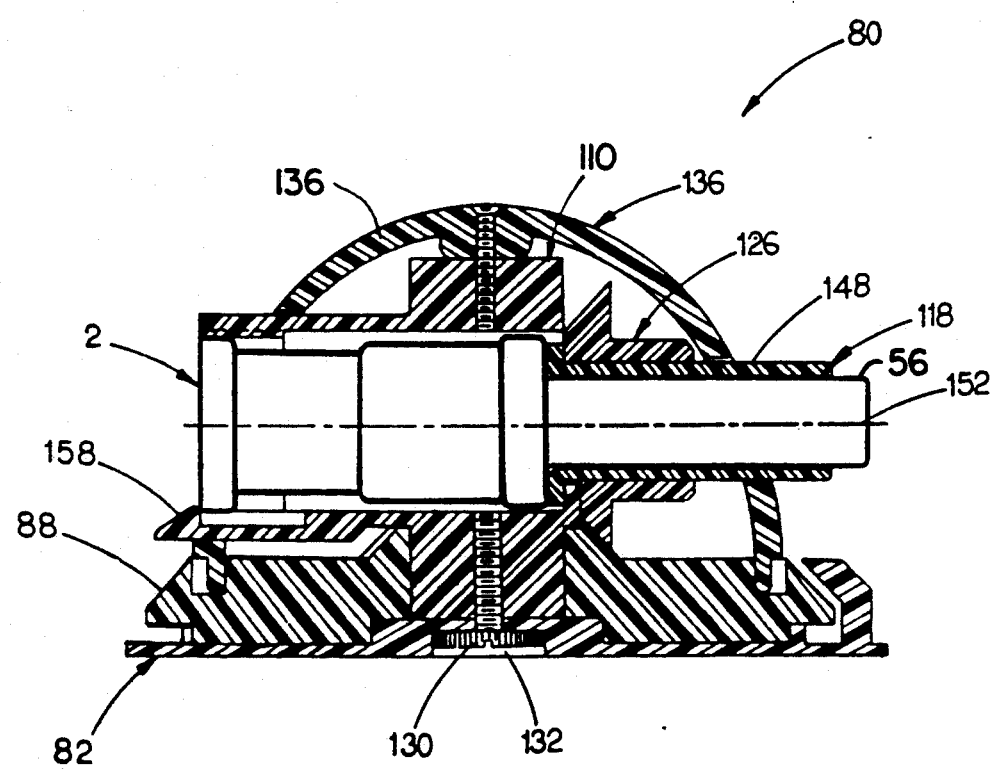
FIG. 7 is a cross-sectional view of a vial assembly, including an external view of the mixing vial of FIG. 3B and a cross-sectional view of the dosing assembly of FIG. 6.

FIG. 7 illustrates dosing assembly 80 housing a mixing vial 2 within the bore 112 of carriage 110 and within the interior 156 of guide drive 118. Interior 156 has an axially extended rib 157 sized to engage one of the several axial grooves 54 formed in syringe holder 50. Mixing vial 2 is held axially within dosing assembly 80 by the engagement of a clip 158, formed integrally with carriage 110, with the outer edge 160 of cup 11. Thus, as guide drive 118 rotates about axis 152, syringe holder 50 also rotates within threaded driver 30 to move syringe holder 50 into mixing container 14, thus driving elastomeric piston 18 down glass cylinder 16, causing mixed pharmaceutical 70 to flow into interior 73 of syringe 4.

An internal rib 164, see FIG. 4D, extending into bore 112 of carriage 110 engages a notched flange 166 on the outside of cup housing 6 to keep the cup housing from rotating within the carriage.

The lower edge 168 of control dome 136 is sized to fit within annular groove 94. As shown in FIGS. 4E, 4F and 4G, control dome 136 includes a pair of resilient, ramped detents 170. Detents 170 engage and are biased radially inwardly by ramped receptacles 95 as control dome 136 (together with carriage 110, guide drive 118 and bevel gear 126) rotates over base 88. The shapes of detents 170 and receptacles 95 are such as to allow control dome 136 to rotate clockwise, that is in the direction of arrow 159 in FIG. 4; counterclockwise rotation for more than one-eighth of a turn (due to the light equally-spaced receptacles 95) is prevented by the engagement of detents 170 and receptacles 95.

In the preferred embodiment threads 36, 52 each have 10 threads per inch (4 threads per cm.) so that one complete rotation of syringe holder 50 causes elastomeric piston 18 to move 0.1 inch 0.25 cm.). Bevel gear 90 has 24 teeth while bevel gear 126 has 24 teeth so that one complete rotation of control dome 136 causes piston 18 to move 0.1 inches 0.25 cm.) corresponding to 8 units of mixed pharmaceutical 70 or 1 cc.

As suggested in FIG. 5, control dome 136 can be decorated. This can be especially helpful if used for administering pharmaceuticals to children, such as growth hormone. If desired, dosing assembly 80 could use a vial which lacks the capability to mix the pharmaceutical but retains the use of syringe holder 50 threadably mounted a threaded adapter or driver similar to mixing vial 2 in the post-mixed condition of FIG. 3B.

Dosing assembly 80 is shown used with mixing vial 2. However, dosing assembly 80 could be used with other pharmaceutical containers which permit access to the pharmaceutical by a hollow needle. For example, a generally conventional cartridge with a movable piston at one end and a septum at the other end could be used; axial movement could be arranged so the piston engages a stationary stop and the barrel is driven over the piston (which is held in place by the stop) by the axial movement of the syringe holder.

Dosing assembly 80 is used by first inserting the smaller end of activated mixing vial 2 (as seen in FIG. 3B) through cut-out 142 of control dome 136 and through the interior 156 of guide drive 118; mixing vial 2 snaps into place as clip 158 engages outer edge 160. Syringe 4 is inserted into the interior 174 of syringe holder 50 until it is fully seated therein with needle cannula 72 passing through piston 18 as shown in FIG. 3C. After first depressing extension 106 in the direction opposite of arrow 159, dosing plate 82 is rotated in the direction of arrow 96. The degree of rotation is both tactilely and aurally indicated through the periodic engagement or attempted engagement limit pin 96 with slots 102. (The degree of rotation of dosing plate 82 about axis 150 can be limited by the use of dose limiter 154 which will engage dome pin 162.) Control dome 136 is then rotated in a counterclockwise direction in FIG. 4. Each one-eighth of a turn is indicated by an audible click when ramped detents 170 pass receptacles 95. This detenting action can also be felt by the user through control dome 136 as well. Control dome 136 is continued to rotate until dome pin 162 contacts extension 106. Since in the preferred embodiment each one-eighth of a revolution corresponds to one unit of mixed pharmaceutical 170, the exact amount of pharmaceutical being transferred into syringe 4 is easily determined and controlled. Syringe 4 is then removed from dosing assembly 80 and the injection is given.

Other modifications and variations can be made to the disclosed embodiment without departing from the subject of the invention as defined in the following claims. For example, although it is preferred that most of the components of mixing vial 2 be made of transparent materials, opaque or translucent materials could be used as well. Dosing assembly 80, with the exception of the screws, is preferably made of opaque plastic, such as styrene, for strength, light weight and durability. Other materials could be used if desired.

What is claimed is:

1. An assembly, for use with a syringe of the type including a body and a hollow needle, for the controlled aspiration of a liquid into the syringe through the needle, the assembly comprising:
   a vial assembly including:
      a container housing a liquid pharmaceutical, having a near open end, a far end and a piston movable within the interior along a path defined between the near and far ends; and
      the container including a pierceable part;
   means for mounting the syringe to the container with the needle piercing the piercable part; and
   driving means rotatable in a first rotary direction about a first axis relative to the container for driving the piston along the pathway so as to force an amount of the liquid pharmaceutical through the needle and into the syringe according to how far the piston is driven along the path;
   a base; and
   means for rotatably mounting the vial assembly to the base for rotational movement of the vial assembly about a second axis generally perpendicular to the base, and means for linking the rotatable mounting means to the driving means so that rotation of the rotatably mounting means about the second axis translates to rotation of the driving means about the first axis to drive the piston.

2. The assembly of claim 1 wherein the piston includes the pierceable part.

3. The assembly of claim 1 wherein the rotatably mounting means includes a vial assembly support.

4. The assembly of claim 3 wherein the linking means includes first and second bevel gears carried by the vial assembly support and the base respectively.

5. The assembly of claim 3 further comprising means for providing an audible indication of the rotation of the vial assembly support about the second axis.

6. The assembly of claim 3 further comprising a dosing plate means, rotatably mounted to the base, for providing a visual indication of the rotation of the vial assembly support about the second axis.

7. The assembly of claim 6 further comprising means for limiting the rotation of the vial assembly support on the base.

8. The assembly of claim 3 wherein the rotatably mounting means includes a control dome mountable to the vial assembly support and rotatable therewith about the second axis.

9. The assembly of claim 8 wherein the control dome and the base include means for providing an audible indication of the relation of the control dome and vial assembly support therewith about the second axis.

10. An assembly, for use with a syringe of the type including a body and a hollow needle, for the controlled aspiration of a liquid into the syringe through the needle, the assembly comprising:
    a vial assembly including:
       a container defining a variable volume region which holds a liquid pharmaceutical, the container including a piercable part providing access to the variable volume region; and
       means for mounting the syringe to the container with the needle piercing the piercable part; and
       means for controllably collapsing the variable volume region, so as to force the liquid pharmaceutical through the hollow needle piercing the piercable part and into the syringe, by rotating at least a part of the controllably collapsing means in a first rotary direction about a first axis;
    a base; and
    means rotatably mounting the vial assembly to the base for rotational movement of the vial assembly about a second axis generally perpendicular to the base, means linking the rotatably mounting means to the controllably collapsing means so that rotation of the rotatably mounting means about the second axis translates to rotation of the said at least part of the controllably collapsing means about the first axis to collapse the variable volume region.

* * * * *